United States Patent [19]

Sato et al.

[11] Patent Number: 5,177,228

[45] Date of Patent: Jan. 5, 1993

[54] PROCESS FOR HYDROFORMYLATION

[75] Inventors: Keiichi Sato, Tokyo; Yuji Kawaragi, Yokohama; Masaki Takai, Setagaya, all of Japan

[73] Assignee: Mitsubishi Kasei Corporation, Tokyo, Japan

[21] Appl. No.: 742,481

[22] Filed: Aug. 5, 1991

Related U.S. Application Data

[63] Continuation of Ser. No. 481,204, Feb. 20, 1990, abandoned.

[30] Foreign Application Priority Data

Jul. 12, 1989 [JP] Japan ................................. 1-179718
Oct. 17, 1989 [JP] Japan ................................. 1-270040

[51] Int. Cl.$^5$ .............................................. C07C 51/10
[52] U.S. Cl. ..................................... 554/129; 554/128; 554/131; 568/451; 568/452; 568/454; 568/882
[58] Field of Search ............... 260/410.9 R; 554/128, 554/129, 131; 568/457, 452, 454, 882, 451, 455

[56] References Cited

U.S. PATENT DOCUMENTS

| 3,954,877 | 5/1976 | Gipson | 568/455 |
|---|---|---|---|
| 4,152,357 | 5/1979 | Poist | 568/455 |
| 4,268,688 | 5/1981 | Tinker et al. | 568/451 |
| 4,482,748 | 11/1984 | Booth | 568/454 |
| 4,506,101 | 3/1985 | Chang | 568/451 |
| 5,917,661 | 11/1975 | Pruett et al. | 568/451 |

OTHER PUBLICATIONS

Chemical Abstracts, vol. 101, #19, 1984, p. 653, 170670q.

*Primary Examiner*—José G. Dees
*Assistant Examiner*—Deborah D. Carr
*Attorney, Agent, or Firm*—Oblon, Spivak, McClelland, Maier & Neustadt

[57] ABSTRACT

Hydroformylation process, wherein an olefinic compound is reacted with hydrogen and carbon dioxide in the presence of a Group VIII precious metal complex catalyst containing an organic phosphorus compound as a ligand, the process being characterized by use of trialkyl phosphine, as the organic phosphorus compound, having the total carbon atom number of 27 or more in its alkyl groups.

22 Claims, No Drawings

PROCESS FOR HYDROFORMYLATION

This application is a continuation of application Ser. No. 07481,204, filed on Feb. 20, 1990 now abandoned.

This invention relates to a process for hydroformylation of an olefinic compound in the presence of a Group VIII precious metal complex catalyst containing a particular organic phosphorus compound as a ligand.

A process, in which aldehyde or alcohol (a hydrogenated product of aldehyde) is produced by reacting the olefinic compound with a mixed gas of $H_2/CO$ in the presence of a soluble organic catalyst of a Group VIII precious metal complex and a phosphorus ligand, has been well known as the hydroformylation process. In this hydroformylation process, the product selectivity, the catalyst reactivity and stability of aldehyde often constitute important factors to be taken into consideration in selecting the phosphorus ligand. In particular, since the catalyst to be used for this purpose is very expensive, it is important from the industrial standpoint to efficiently separate and recover the catalyst from the liquid reaction product, and return it to the reaction system again.

When the reaction product obtained from the hydroformylation reaction is of a relatively low boiling point, the reaction product and the catalyst liquid can usually be separated and recovered by distillation, the catalyst liquid being able to be re-circulated into the hydroformylation reaction.

In the hydroformylation reaction, however, various high boiling point products are yielded as by-products, on account of which the high boiling point by-products are progressively accumulated in the reaction system by the re-circulation of the catalyst liquid with the consequent inability to secure the stable operation.

In order to solve this problem, it is necessary that the high boiling point by-product be removed from the catalyst liquid by distillation. However, even this treatment has a problem such that the above-mentioned complex undergoes heat-deterioration at a temperature as high as 150° C. or above to bring about decrease in the catalytic activity (vide: Japanese Unexamined Patent Publication No. 196537/1988).

Further, when the reaction product has a high boiling point, in particular, when it has a relatively poor heat-stability, which is derived from use of higher unsaturated fatty acids or their esters, etc. as the starting material, a high temperature is required to separate the reaction product and the catalyst liquid for their recovery, on account of which there still remains a problem such that not only the reaction product is decomposed or lost to be the high-boiling by-products, but also the catalytic activity of the catalyst becomes lowered due to heat-deterioration.

As the measures for solving these problems, there has been proposed other methods of recovery than distillation, wherein the Group VIII precious metal complex soluble with organic phosphorus compound or the Group VIII precious metal is recovered by means of, for example, adsorption, extraction and so forth. Examples of such proposed methods are as follows.

1) Liquid of a reaction product obtained by hydroformylation of methyl oleate in the presence of triphenyl phosphite and a rhodium catalyst carried on an alumina carrier is filtered to separate the same into the alumina carrier and the filtered liquid. Then, the filtered liquid is further separated by distillation into the reaction product and the soluble rhodium catalyst. The thus separated soluble rhodium catalyst is then carried on the above-mentioned alumina carrier, and activated by baking so as to be used again for the hydroformylation reaction (vide: Journal of the American Oil Chemical Society, 50, pp 455~458 (1973)).

2) Unsaturated fatty acid compound is subjected to the hydroformylation reaction in the presence of a complex catalyst consisting of a Group VIII precious metal and an organic phosphorus compound, and the reaction liquid as obtained is brought into contact with an activated carbon adsorbent, on which the organic phosphorus compound is carried, thereby adsorbing the complex body on the adsorbent. After this, the reaction liquid is brought into contact with the desorbed liquid to elute the complex body which is adsorbed on the adsorbent, while the isolated organic phosphorus compound is recovered by distillation from the reaction liquid after the above-mentioned adsorption treatment. The recovered organic phosphorus compound is combined with the above-mentioned eluted complex body to be used again in the hydroformylation reaction (vide: Japanese Unexamined Patent Publication No. 196537/1988).

The above-mentioned method 1) is difficult to be adopted for the purpose of the industrialized process for the reasons that the organic phosphorus compound to be added as the ligand cannot be recovered by this method; its recovery work is complicated; and, from the standpoint of the hydroformylation reaction per se, a large amount of rhodium is necessary for the hydroformylation reaction to proceed at an appropriate rate of reaction and a rate of yield, which accompanies industrial disadvantage.

On the other hand, while the above-mentioned method 2) indicates a high rate of recovery of the catalyst and the isolated organic phosphorus compound, the method has been found to be low in the catalytic activity in the low pressure reaction zone, when the hydroformylation reaction was carried out with the method 2) by the present inventors, as will be shown later in comparative examples.

In view of these actual situations with the abovementioned conventional techniques, the present inventors have conducted studies and repeated experiments to find out an industrially advantageous hydroformylation process, by which the hydroformylated product can be obtained from an olefinic compound at a high rate of yield, even in a low pressure reaction zone, and yet the catalyst used for the reaction can be efficiently recovered from the reaction product, and recycled to the reaction system. As the result of such strenuous efforts, they have arrived at the present invention.

According to the present invention, use of the Group VIII precious metal complex catalyst containing a specific organic phosphorus compound as the ligand makes it possible to obtain the hydroformylated product at an appropriate rate of reaction and a very high rate of yield, even under a low pressure reaction condition, and, moreover, stability of the catalyst increases, which makes it possible to maintain very high catalytic activity, even when the catalyst is separated for recovery by distillation at a temperature as high as, for example, 150° C. or above, and then recirculated to the reaction system for the hydroformylation without subjecting it to any particular activation treatment.

That is to say, the gist of the present invention resides in the hydroformylation process, wherein an olefinic compound is reacted with hydrogen and carbon monoxide in the presence of a Group VIII precious metal complex catalyst containing an organic phosphorus compound as a ligand, which process is characterized by the use of trialkyl phosphine as the above-mentioned organic phosphorus compound having the total carbon atom number of 27 or more in its alkyl group.

In the following, the present invention will be described in specific details.

There is no particular limitation to the olefinic compound to be used as the reaction material in the process of the present invention, provided that it is an organic compound having at least one olefinic double bond within its molecule. Examples of such olefinic compound are: olefinic hydrocarbons such as ethylene, propylene, butene, butadiene, octene, octadiene, dodesene, octadesene, eicosene, docosene, styrene, cyclohexene and mixtures of isomers of olefinic oligomers such as lower olefinic dimers, trimers and tetramers of propylene, n-butene, isobutylene, and others; and substituted olefins like acrylonitrile, allylalcohol, 1-hydroxy-2,7-octadiene, 3-hydroxy-1,7-octadiene, methyl acrylate, oleyl alcohol, unsaturated fatty acid compounds, and so forth.

One of the characteristics of the present invention is that it is applicable to a case where the starting materials of high boiling point such as octadesene, eicosene, docosene, and other higher olefinic hydrocarbons, higher substituted olefins such as oleyl alcohol and higher unsaturated fatty acid compounds, and so forth are used, hence the reaction product to be obtained is of a high boiling point.

As the above-mentioned unsaturated fatty acid compounds to be one of the starting materials for the reaction process according to the present invention, there may be exemplified those higher unsaturated fatty acids and their esters to be produced in the form of animal fat and vegetable oil. As the unsaturated fatty acid esters, there may usually be used esters of unsaturated fatty acid and a monovalent alcohol.

Examples of such unsaturated fatty acid compounds are: mono-unsaturated fatty acid having the carbon content of from 16 to 18, such as palmitoleic acid, oleic acid, etc. which are present in the nature in a relatively large quantity; esterified substances of mono-unsaturated fatty acid having the carbon content of from 16 to 18, such as methyl palmitoleate, methyl oleate, ethyl oleate, etc.; and others.

By the way, it is difficult to obtain industrially these mono-unsaturated fatty acid compounds (such compound will hereinafter be simply referred to as "mono-ene"). These are usually available in the form of a mixture of various fatty acid compounds having wide distribution of carbon content and different degree of unsaturation.

In accordance with the process of the present invention, it is possible to satisfactorily hydroformylate those mixtures of the fatty acid compounds having such wide distribution of carbon content and different degree of unsaturation. Of these mixtures of the unsaturated fatty acid compounds, use of the mixtures with limited content of the unsaturated fatty acid compound having two or more carbon-to-carbon double bonds in the molecule (such compound will hereinafter be simply referred to as "poly-ene"), as the starting material, for the hydroformylation is desirable in the production of the formylated substance at a favorable rate of reaction and with a high rate of yield.

More particularly, it is most suitable to use the mixtures with the content of the "poly-ene" at the time of the hydroformylation being approximately 20% by weight or below, more preferably 10% by weight or below, with respect to the total quantity of the "mono-ene" and the "poly-ene".

In this case, the content of the "poly-ene" can be regulated by pre-treating, in advance of the hydroformylation, the mixture of these unsaturated fatty acids by the selective hydrogenation method, etc. to convert the "poly-ene" to the "mono-ene".

By the way, at the time of hydroformylation of the "poly-ene" containing "mono-ene" by its reaction with hydrogen and carbon monoxide in the presence of the rhodium catalyst, if the "poly-ene" is in a quantity of by weight or below with respect to the total quantity of both mono-ene and poly-ene, or preferably in a range of from 0.005 to 5% by weight, or more preferably from 0.01 to 4% by weight, or optimumly from 0.05 to 3% by weight, it is possible to obtain the hydroformylated substance at an appropriate rate of reaction and a high rate of yield, even with a relatively low concentration of the rhodium catalyst, which ranges from $1.4 \times 10^{-5}$ to $1.9 \times 10^{-2}\%$ by weight with respect to the total quantity of the mono-ene and the poly-ene, or preferably from $1.4 \times 10^{-4}$ to $1.7 \times 10^{-2}\%$ by weight, in terms of a converted value of Rh atom.

The Group VIII precious metal complex containing the organic phosphorus compound as the ligand can be readily prepared from the Group VIII precious metal compounds and the organic phosphorus compounds to be described later, by a well known complex forming method. In this case, those ligands other than the organic phosphorus compounds, such as the acetyl acetonate group, the cyclopentadienyl group, the carbonyl group, the carboxyl group, halogens, and hydrogen may further be contained in this complex.

As the Group VIII precious metal compounds to be used for forming the complex, there may be exemplified oxides, halides, inorganic acid salts, organic acid salts, hydrides, carbonyl complexes, amine complexes, etc., of the Group VIII precious metals such as cobalt, rhodium, ruthenium, palladium, osmium, iridium, platinum, and so on. Of these compounds, the rhodium compounds are of particular importance.

Examples of the rhodium compounds are: rhodium nitrate, rhodium sulfate, rhodium trichloride, rhodium oxide, and other inorganic compounds of rhodium; rhodium acetate, and other organic acid salts of rhodium; $Rh(acac)_3$, $Rh(acac)(CO)_2$, $[Rh(OAc)COD]_2$, $Rh_4(CO)_{12}$, $HRh(CO)(PPh_3)_3$; and various other rhodium complexes. (In these chemical formulas, "acac" denotes the acetyl acetonate group; "Ac" represents the acetyl group; "COD" refers to 1,5-cyclo-octadiene; and "Ph" denotes the phenyl group.)

The quantity of use of the Group VIII precious metal compounds is not particularly limited. While there may exist a certain limitation to be taken into consideration from the catalytic activity and economy of such catalyst compounds, the quantity can be so selected that, for the purpose of the present invention, the concentration of the compound in an ordinary reaction zone may be in a range of from $1.2 \times 10^{-5}$ to $1.2 \times 10^{-1}\%$ by Weight, or preferably from $1.2 \times 10^{-4}$ to $3.5 \times 10^{-2}\%$ by weight, with respect to the total quantity of the olefinic compound, in terms of the converted value of the Group VIII precious metal.

The organic phosphorus compound to be used in the present invention is trialkyl phosphine having the carbon content of 27 or more in its alkyl group. This trialkyl phosphine can be represented by the following general formula,

(where: $R_1$, $R_2$ and $R_3$ respectively denote the alkyl group, and the total carbon atom number in these $R_1$, $R_2$ and $R_3$ are 27 or more).

Of various trialkyl phosphines as represented above, those having the carbon atom number of at least 6 in each of these three alkyl groups are more preferable.

When the total carbon atom number in the above-mentioned alkyl groups is below 27, the rate of the hydroformylation reaction is low, hence the reaction results of the catalyst at the time of its recycled use, after separation of the hydroformylated product and the catalyst by distillation, become also poor.

The above-mentioned upper limit of the total carbon atom number in the alkyl groups is not limitative. Although there is no necessity for increasing the carbon atom number more than that, with which the process of the present invention can be carried out efficiently, when the carbon content becomes excessively large, the solubility of the organic phosphorus compound becomes lowered, hence it is appropriately selected in such a manner that the reaction liquid may be rendered a uniform solution under the conditions for the hydroformylation reaction. That is, the carbon content of 90 or below, or more preferably 70 or below, should be sufficient for the purpose of the present invention.

Concrete examples of the organic phosphorus compounds to be used in the present invention are as follows: tri-n-nonyl phosphine, tri-n-decyl phosphine, tri-isodecyl phosphine, mixtures of tri-decyl phosphine, tri-n-dodecyl phosphine, tri-n-tetradecyl phosphine, di-n-dodecyl tetradecyl phosphine, tri-n-octadecyl phosphine, tri-ndocosyl phosphine, di-n-hexyl octadecyl phosphine, di-n-dodecyl-n-hexyl phosphine, and so forth. Of these compounds, tri-n-decyl phosphine, tri-n-dodecyl phosphine, tri-n-tetradecyl phosphine, and tri-noctadecyl phosphine are particularly preferable.

There is no particular limitation to the quantity of use of the above-mentioned organic phosphorus compound, but it can be arbitrarily selected in such a manner that a desired result may be obtained for the sake of the catalytic activity and the catalytic stability. Usually, its quantity is selected in a range of from about 1 to 500 mols, or preferably from 2 to 100 mols per 1 mol of rhodium atom.

In carrying out the hydroformylation reaction by the process of the present invention, use of a reaction solvent is not essential. If necessary, however, a solvent which is inactive to the hydroformylation reaction may be present in the reaction system. Examples of the preferred solvents are: aromatic hydrocarbon compounds such as toluene, xylene, dodecylbenzene, etc.; ketones such as acetone, diethyl ketone, methylethyl ketone, and so forth; ethers such as tetrahydrofuran, dioxane, and so on; and esters such as ethyl acetate, di-n-octylphthalate, and so on.

The reaction conditions for the hydroformylation reaction in the process of the present invention may be the same as those which have usually been employed, wherein the reaction temperature is selected in a range of from room temperature to 200° C., or preferably from 50° C. to 150° C.; the reaction pressure is selected from a range of from a normal pressure to 200 atmospheres, or preferably from 5 to 100 atmospheres, or more preferably from 5 to 50 atmospheres.

The molar ratio between hydrogen and carbon monoxide ($H_2/CO$) is usually selected in a range of from 10/1 to 1/10, or preferably from 1/1 to 6/1. The hydroformylation reaction can be done either continuously or batch-wise in an agitation-type reaction vessel or a foaming-tower type reaction vessel.

Separation of hydroformylated product and the catalyst liquid from the liquid of the hydroformylation reaction, at the time of effecting the process of the present invention may be done by the well known methods such as the ordinary vacuum distillation or the thin film molecular distillation. There is no particular limitation to the conditions for the distillation, but it can be arbitrarily established so as to obtain the desired result, while taking into consideration the volatile property and the heat-stability of the resulting hydroformylated product, and the volatile property, heat-stability, etc. of the catalyst containing therein the isolated organic phosphorus compound. In general, a temperature range of from 50° C. to 300° C. and a pressure range of from 760 mmHg to $10^{-4}$ mmHg may be usually selected.

In carrying out the distillation, use of the solvent is not essential. If required, however, a solvent which is inactive to the hydroformylated product and the catalyst may be present in the reaction system. From the residual liquid containing therein the isolated catalyst, the Group VIII precious metals can be recovered by the well known method, or at least a part of the residual liquid is circulated into the reaction steps for the hydroformylation so as to be able to use the catalyst again.

In the following, the present invention will be described in further details with reference to several preferred examples thereof. It should, however, be noted that these examples are merely illustrative of the present invention and not so restrictive, and that any changes and modifications may be made by those persons skilled in the art without departing from the spirit and scope of the invention, as recited in the appended claims.

EXAMPLE 1

Into a stainless steel autoclave of up-and-down agitation type, having an internal capacity of 200 ml, the following ingredients for the hydroformylation reaction were charged, in a nitrogen atmosphere: 60 ml of crude methyl oleate as the starting material (composed of 85.34% by weight of methyl oleate, 11.29% by weight of methyl stearate, 0.17% by weight of methyl hexadecanate, 2.66% by weight of methyl palmitate, and 0.2% by weight or below of methyl rinolate); 5 ml of n-tetradecane; 15.5 mg of Rh(acac)(CO)$_2$; and 5 mols of P(n-C$_{12}$H$_{25}$)$_3$ per 1 mol of rhodium atom. After the charging of these ingredients, the autoclave was tightly closed. Then, nitrogen gas was filled into this autoclave under pressure of up to and including 10 kg/cm$^2$G. Thereafter, operation of returning the pressure level to a normal pressure was repeated for three times, after which the temperature in the autoclave was elevated to 130° C. As soon as the temperature reached 130° C., water gas ($H_2/CO=1$) was promptly sent into the autoclave under pressure so that the total pressure might become 50 kg/cm$^2$G, and the reaction was commenced, which was continued for two hours. The water gas, which was consumed by the reaction, was replenished by a pressure accumulator through a constant pressure device, thereby maintaining the reaction pressure at a constant level of 50 kg/cm$^2$G.

After the reaction, the reaction liquid was taken out of the autoclave and concentration of the reaction product was measured by its analyses through a gas chromatograph (column: "Thermon-3000", capillary: 0.25 mm$\Phi$ ×50m), are shown in Table 1 below.

Subsequently, the resulted reaction liquid was charged into a funnel of a flowing type thin film distillation device, in an argon atmosphere, after which the distillation was commenced at a temperature of 235° C. (a temperature of a reflux steam generating source) and under a reduced pressure of 4 mmHg. After the distillation, 60 ml of the above-mentioned crude methyl oleate as the starting material and 5 ml of n-tetradecane were added, in an argon atmosphere, to a small quantity of the residual liquid contained in the catalyst liquid, and then the batch was transferred into a stainless steel autoclave of up-and-down agitation type, having an internal capacity of 200 ml, the interior of which had been substituted with argon. Subsequently, the second reaction was effected by the same operation as done in the above-mentioned initial reaction. The results of the gas chromatographic analyses after the reaction are also shown in Table 1 below.

EXAMPLE 2

The same procedures as in Example 1 above were followed, with the exception that use was made of P(n-C$_{10}$H$_{21}$)$_3$ in place of P(n-C$_{12}$H$_{25}$)$_3$. The results of the gas chromatographic analyses after the reaction are Shown in Table 1 below.

EXAMPLES 3 and 4

The same procedures as in Example 1 above were followed with the exception that, in place of P(nC$_{12}$H$_{25}$)$_3$, P(n-C$_8$H$_{17}$)$_3$ was used in Example 3, and P(C$_6$H$_5$)$_3$ was used in Example 4. The results Of the gas chromatographic analyses after the reaction are shown in Table 1 below.

TABLE 1

| Ex. No. | Organic phosphorus ligand | Number of reaction | Results of reaction (mol %) | | | *4Rate of reaction (mol/l · hr) |
|---|---|---|---|---|---|---|
| | | | Invert ratio of *1MO + ML | Rate of yield of *2MSF | Rate of yield of *3MS | |
| 1 | P(n-C$_{12}$H$_{25}$)$_3$ | first | 97.3 | 94.8 | 2.4 | 7.67 |
| | | second | 98.8 | 96.3 | 2.5 | 8.81 |
| 2 | P(n-C$_{10}$H$_{21}$)$_3$ | first | 97.5 | 94.9 | 2.6 | 7.28 |
| | | second | 98.5 | 96.1 | 2.4 | 8.92 |
| 3 | P(n-C$_8$H$_{17}$)$_3$ | first | 96.8 | 94.2 | 2.6 | 6.72 |
| | | second | 84.8 | 83.4 | 1.7 | 2.27 |
| 4 | P(C$_6$H$_5$)$_3$ | first | 72.7 | 70.4 | 1.0 | 2.88 |
| | | second | — | — | — | — |

*1MO: methyl oleate. ML: methyl rinolate invert ratio = $\frac{\text{charged [MO + ML]} - \text{unreacted [MO + ML]}}{\text{charged [MO + ML]}} \times 100$ (mol %)

*2MFS: methylformyl stearate rate of yield = $\frac{\text{produced MFS}}{\text{charged [MO + ML]}} \times 100$ (mol %)

*3MS: methyl stearate rate of yield = $\frac{\text{produced MS}}{\text{charged [MO + ML]}} \times 100$ (mol %)

*4primary approximate speed in a range of the invert ratio of from 0 to 50%

EXAMPLE 5

The same procedures as in Example 1 above were followed, with the exception that the quantities of use of Rh(acac)(CO)$_2$ and P(n-C$_{12}$H$_{25}$)$_3$ were respectively made 30.0 mg and 4 mols per 1 mol of rhodium atom, the reaction pressure was made 8.5 kg/cm$^2$G, and the reaction time was made 5 hours to carry out the hydroformylation reaction for only one time. Table 2 below shows the results of the gas chromatographic analyses after the reaction.

EXAMPLES 6 and 7

The same procedures as in Example 5 above were followed with the exception that, in place of P(n-C$_{12}$H$_{25}$)$_3$ in Example 5, P(n-C$_2$H$_5$)$_3$ was used in Example 6, and P(C$_6$H$_5$)$_3$ was used in Example 7. The results of the gas chromatographic analyses after the reaction are shown in Table 2 below.

TABLE 2

| Ex. No. | Organic phosphorus ligand | Reaction results (mol %) | | | Rate of reaction (mol/l · hr) |
|---|---|---|---|---|---|
| | | Invert ratio of MO + ML | Rate of yield of MSF | Rate of yield of MS | |
| 5 | P(n-C$_{12}$H$_{25}$)$_3$ | 96.9 | 93.5 | 2.3 | 1.54 |
| 6 | P(n-C$_2$H$_5$)$_3$ | 61.1 | 59.4 | 1.0 | 0.31 |
| 7 | P(C$_6$H$_5$)$_3$ | 4.7 | 5.8 | 1.1 | — |

EXAMPLE 8

Into a stainless steel micro-autoclave of spinner-agitation type, having an inner capacity of 70 ml the following ingredients were charged in an argon gas atmosphere: 21.08 g of 1-docosene, 3 ml of n-tetradecane, 14.7 mg of Rh(acac)(CO)$_2$, and 5 mols of P(n-C$_{12}$H$_{25}$)$_3$ per 1 mol of rhodium atom. After the charging, the autoclave was tightly closed, and argon gas was filled thereinto under a pressure of upto and including 10 kg/cm$^2$G. Thereafter, operation of returning the pressure within the autoclave to a normal pressure was repeated for three times, and then the temperature was elevated to 130° C. As soon as the temperature reached the level of 130° C., water gas (H$_2$/CO=1) was filled under pressure so as to bring the total pressure to 7.5 kg/cm$^2$, and the reaction was effected for three hours, while maintaining the pressure at 7.5 kg/cm$^2$G constant. After the reaction for 3 hours, the reaction liquid was drained in a state of its being heated at 50° C. to subject the reaction product to the gas chromatographic analyses. Table 3 below shows the results of the analyses (the invert ratio of olefin, rate of yield of produced aldehyde, and ration of parafination). In the next place, the resulted reaction liquid in the state of its having been heated to 50° C. was charged, in the argon gas atmosphere, into a thin film distillation device, and the distillation was carried out under the same conditions as in Example 1 above. After the distillation, 21.10 g of 1-docosene and 3 ml of n-tetradecane were again added to a small amount of residual liquid containing therein the catalyst liquid, and the second reaction was conducted by the same manner of operation as in the first reaction. Table 3 below indicates the results of the gas chromatographic analyses of the drained liquid after the reaction.

EXAMPLE 9

The same procedures as in Example 8 above were followed, with the exception that, in place of P(nC$_{12}$H$_{25}$)$_3$ in Example 8, (n-C$_8$HI$_7$)$_3$ was used. The results of the gas chromatographic analyses after the first and second oxo-reaction are shown in Table 3 below.

EXAMPLE 10

The same procedures as in Example 8 above were followed with the exception that, in place of 1-docosene in Example 8, 27 ml of oleyl alcohol (purity: 87.4 wt.%) was used, and the reaction was conducted for 5 hours (provided that, after the oxo-reaction, heating of the reaction liquid at the time of the analyses and the distillation was omitted). The results of the gas chromatographic analyses (column; 5% PEG-HT/Uniport-P) after the first and second oxo-reaction are shown in Table 3 below.

EXAMPLE 11

The same procedures as in Example 10 above were followed with the exception that, in place of P(n-C$_{12}$H$_{25}$)$_3$ in Example 10, (n-C$_8$H$_{17}$)$_3$ was used. The results of the gas chromatographic analyses after the oxo-reaction are shown in Table 3 below.

TABLE 3

| Ex. No. | Olefin | Organic phosphorus ligand | Number of reaction | Results of reaction (mol %) | | |
|---|---|---|---|---|---|---|
| | | | | Olefin invert ratio | Rate of yield of aldehyde | Rate of paraffinizing |
| 8 | 1-Docosene | P(n-C$_{12}$H$_{25}$)$_3$ | first | 99.5 | 95.8 | 1.3 |
| | | | second | 99.6 | 94.6 | 1.5 |
| 9 | 1-Docosene | P(n-C$_8$H$_{17}$)$_3$ | first | 99.0 | 95.3 | 1.3 |
| | | | second | 87.4 | 84.5 | 1.6 |
| 10 | Oleyl alcohol | P(n-C$_{12}$H$_{25}$)$_3$ | first | 68.3 | 65.5 | 1.3 |
| | | | second | 70.2 | 66.5 | 1.6 |
| 11 | Oleyl alcohol | P(n-C$_8$H$_{17}$)$_3$ | first | 67.6 | 65.0 | 1.5 |
| | | | second | 45.3 | 43.1 | 1.1 |

EXAMPLE 12

Preparation of a mixture of unsaturated aliphatic acid compounds 150 ml of crude methyl oleate ester available in general market (material a in Table 4 below) and 1.50 g of 1% Pd/Al$_2$O$_3$ powder catalyst were charged into a stainless steel autoclave of induction-agitating type, having an inner capacity of 200 ml, and then it was tightly closed. After this, nitrogen gas was further filled into this autoclave under pressure of upto and including 10 kg/cm$^2$G. After repeating the operation of returning the pressure to a normal level for three times, the temperature within the autoclave was raised to 100° C. As soon as the temperature reached 100° C., the hydrogenation reaction was conducted, while intermittently feeding hydrogen gas under a pressure of 5 kg/cm$^2$G or below. On the way of this hydrogenation reaction, the content in the reaction system was sampled for analysis through a gas chromatograph, thereby pursuing the reaction. Upon completion of the hydrogenation reaction, the catalyst was separated from the reaction system with use of a 0.8μ-membrane filter. By effecting the above-mentioned hydrogenation reaction for an appropriate length of time, there were prepared mixtures of materials with different contents of the poly-enes (materials b and c in Table 4 below). Also, after refining of the material a by distillation, the hydrogenation reaction was conducted in the same manner as mentioned above, thereby obtaining mixtures of materials having different contents of the poly-enes (materials d and e in Table 4).

Besides the above, methyl rinolate available in general market was added to the material d to prepare mixtures of materials with different contents of the poly-enes (materials f and g in Table 4 below).

TABLE 4

| Material | | | a | b | c | d | e | f | g |
|---|---|---|---|---|---|---|---|---|---|
| Unsaturated fatty acid compound | Mono-ene | C$_{13}^1$ = COOME | 0.51 | 0.51 | 0.51 | — | — | — | — |
| | | C$_{15}^1$ = COOMe | 5.24 | 5.24 | 5.24 | — | — | — | — |
| | | C$_{16}^1$ = COOMe | 0.98 | 0.98 | 0.98 | — | — | — | — |
| | | C$_{17}^1$ = COOMe | 77.27 | 81.73 | 80.56 | 87.57 | 79.19 | 81.18 | 81.54 |
| | Poly-ene | C$_{17}^2$ = COOMe | 5.48 | 1.19 | 2.35 | 0.35 | 0.06 | 3.94 | 4.64 |
| | | C$_{17}^3$ = COOMe | 0.17 | Trace | Trace | Trace | Trace | Trace | Trace |
| Saturated fatty acid methyl ester | | | 10.35 | 10.36 | 10.35 | 12.08 | 20.75 | 14.88 | 13.82 |

EXAMPLES 13 to 18

Into a stainless steel autoclave of up-and-down agitation type, having an inner capacity of 200 ml, the following ingredients were charged in a nitrogen atmosphere: 60 ml of the material b obtained in Example 12

(vide: Example 14), the material c (vide: Examples 13 and 18), the material e (vide: Example 15), the material f (vide: Example 16), or the material g (vide: vide Example 17): 5 ml of m-xylene; and methanol solution of rhodium acetate in a quantity sufficient to attain a predetermined rhodium concentration (1.374 mg of metallic rhodium in 1 g of methanol), and then it was tightly closed. Nitrogen gas was further filled into this autoclave under pressure of upto and including 10 kg/cm$^2$G, after which, the operation of returning the pressure to a normal level was repeated for three times. Thereafter, temperature within the autoclave was raised to 130° C. As soon as the temperature reached 130° C., water gas (H$_2$/CO=1) was filled into the autoclave under pressure such that the total pressure therewithin might become 170 kg/cm$^2$G, and the reaction was commenced, which was continued at this temperature level for a time period as indicated in Table 5 below. The water gas, which was consumed by the reaction, was replenished from pressure accumulator through a constant pressure device, thereby maintaining the reaction pressure at the constant level of 170 kg/cm$^2$G. After the reaction, test specimens were taken out of the reaction system to measure the concentration of the reaction product by the gas chromatographic analyses. The results are shown in Table 5 below.

EXAMPLES 19 to 22

The same procedures as in Example 13 above were followed, with the exception that, in place of the material c, use was made of 60 ml of methyl oleate ester available in general market (the material a in Table 4) to carry out the reaction under the conditions as shown in Table 5 below. The results of the gas chromatographic analyses of the reaction product after the reaction are shown in Table 5 below.

EXAMPLE 23

The same procedures as in Example 13 above were followed, with the exception that 60 ml of the material d obtained in Example 12, 5 ml of m-xylene, methanol solution of rhodium acetate in a quantity sufficient to attain the rhodium concentration as shown in Table 6 below, and triphenyl phosphine as shown in Table 6 were charged into a stainless steel autoclave having an inner capacity of 200 ml, and the reaction was conducted for 1.5 hours. The results of the gas chromatographic analyses on the reaction product after the reaction are shown in Table 6 below.

TABLE 6

| Example No. | Rh concentration (wt %) | PΦ$_3$*$^1$/Rh (mol/mol) | Material | Content of poly-ene in material (wt %) | Reaction time (hr) | Invert ratio (MO + ML) | Rate of yield (MFS) |
|---|---|---|---|---|---|---|---|
| 23 | 0.0014 | 30 | d | 0.40 | 1.5 | 93.5 | 93.0 |

*$^1$PΦ$_3$ represents triphenyl phosphine.

As has so far been described in the foregoing, the method of the present invention is capable of effecting hydroformylation of olefinic compounds with good efficiency and high rate of yield. In particular, it is capable of satisfactorily effecting the hydroformylation of higher olefinic compounds, even under low pressure conditions.

We claim:
1. A hydroformylation process, comprising:
reacting an olefinic compound with hydrogen and carbon monoxide in the presence of a catalyst of a rhodium complex containing having three identical alkyl groups, wherein the total carbon atom content in the alkyl groups of said trialkylphosphine is 27 or more.
2. A hydroformylation process, comprising:
reacting an olefinic hydrocarbon or a substituted olefin with hydrogen and carbon monoxide in the presence of a catalyst containing a rhodium complex and a trialkylphosphine having three identical alkyl groups, wherein the total carbon atom content in the alkyl groups of said trialkylphosphine is 27 or more optionally in a solvent.

TABLE 5

| Example No. | Rh concentration*$^1$ (wt %) | Material | Content of poly-ene in material [Poly-ene/(Mono-ene + Poly-ene)] (wt %) | Reaction time (hr) | Invert ratio (MO + ML)*$^2$ | Rate of yield (MFS)*$^3$ |
|---|---|---|---|---|---|---|
| 13 | 0.0145 | c | 2.62 | 2 | 94.0 | 93.5 |
| 14 | 0.0015 | b | 1.33 | 4 | 94.4 | 94.0 |
| 15 | 0.0145 | e | 0.08 | 2 | 98.2 | 97.5 |
| 16 | 0.0151 | f | 4.63 | 2 | 58.8 | 58.2 |
| 17 | 0.0150 | g | 5.38 | 2 | 35.0 | 34.6 |
| 18 | 0.0165 | c | 2.62 | 2 | 95.0 | 94.1 |
| 19 | 0.0365 | a | 6.30 | 2 | 89.9 | 88.8 |
| 20 | 0.0145 | a | 6.30 | 2 | 12.1 | 12.0 |
| 21 | 0.0015 | a | 6.30 | 4 | 2.0 | 2.0 |
| 22 | 0.0165 | a | 6.30 | 2 | 14.6 | 14.0 |

*$^1$Rh concentration with respect to the total quantity of unsaturated fatty acid compounds in each material
*$^2$MO: methyl oleate, ML: methyl rinolate $$\text{invert ratio} = \frac{\text{charged [MO + ML] - unreacted [MO + ML]}}{\text{charged [MO + ML]}} \times 100 \text{ (mol \%)}$$

*$^3$MFS: methylformyl stearate $$\text{rate of yield} = \frac{\text{produced MFS}}{\text{charged [MO + ML]}} \times 100 \text{ (mol \%)}$$

3. The process of claim 2, wherein said trialkylphosphine contains from 27 to 90 carbon atoms.

4. The process of claim 2, wherein said trialkylphosphine is a member selected from the group consisting of tri-n-decyl phosphine, tri-n-dodecyl phosphine, tri-n-tetradecyl phosphine and tri-n-octadecyl phosphine.

5. The process of claim 2, wherein said olefinic hydrocarbon is ethylene, propylene, butene, butadiene, octene, octadiene, dodesene, octadesene, eicosene, docosene, styrene, cyclohexene, or mixtures of isomers of olefinic oligomers of lower olefins.

6. The process of claim 5, wherein said oligomers of lower olefins are dimers, trimers and tetrimers.

7. The process of claim 2, wherein said substituted olefin is acrylonitrile, allyl alcohol, 1-hydroxy-2,7-octadiene, 3-hydroxy-1,7-octadiene, methyl acrylate, oleyl alcohol or an unsaturated fatty acid compound.

8. The process of claim 7, wherein said substituted olefin is an unsaturated fatty acid compound.

9. The process of claim 8, wherein said unsaturated fatty acid compound is a member selected from the group consisting of mono-unsaturated aliphatic acids having a carbon atom number content of from 16 to 18 and esters thereof.

10. The process of claim 8 or 9, wherein said unsaturated fatty acid compound is a mixture of unsaturated fatty acids in which 20% by weight or less of the unsaturated acids contain two or more double bonds with the remainder of the unsaturated acids being mono-unsaturated aliphatic acid compounds.

11. The process of claim 2, wherein the concentration of said rhodium metal element in the hydroformylation reaction zone is within the range of from $1.2 \times 10^{-5}$ to $1.2 \times 10^{-1}$% by weight with respect to the total quantity of olefinic compound in the medium in terms of a converted value of said rhodium metal.

12. The process of claim 2, wherein the quantity of said trialkylphosphine ligand ranges from 1 to 500 moles per one mole of rhodium.

13. The process of claim 2, wherein the amount of said trialkylphosphine, ranges from 2 to 100 moles per 1 mole of rhodium.

14. The process of claim 2, wherein the reaction medium in which the hydroformylation reaction occurs contains a solvent which is inactive to the hydroformylation reaction conditions.

15. The process of claim 14, wherein said reaction solvent is an aromatic hydrocarbon compound, a ketone or ester.

16. The process of claim 2, wherein the hydroformylation reaction is conducted at a temperature ranging from room temperature to 200° C.

17. The process of claim 2, wherein the hydroformylation reaction is conducted under a pressure ranging from ambient pressure to 200 atm.

18. The process of claim 2, wherein the product of hydroformylation and catalyst containing liquid are separated from the hydroformylation reaction medium by distillation.

19. The process of claim 18, wherein said distillation is vacuum distillation or thin film distillation.

20. The process of claim 18, wherein said distillation is conducted at a temperature ranging from 50° to 300° C. under a pressure ranging from 760 mmHg to $10^{-4}$ mmHg.

21. The process of claim 18, wherein said catalyst containing liquid separated by distillation is recirculated to the hydroformylation reaction medium for repeated use.

22. The process of claim 2, wherein the molar ratio of hydrogen to carbon monoxide ranges from 10/1 to 1/10.

* * * * *